United States Patent [19]

Rattenborg

[11] 4,340,067
[45] Jul. 20, 1982

[54] BLOOD COLLECTION SYRINGE

[76] Inventor: Christen C. Rattenborg, 1379 E. 55th Pl., Chicago, Ill. 60637

[21] Appl. No.: 135,314

[22] Filed: Mar. 31, 1980

[51] Int. Cl.³ .................................................. A61B 5/14
[52] U.S. Cl. .................................. 128/763; 128/218 PA
[58] Field of Search ......... 128/218 P, 218 PA, 218 R, 128/218 M, 215, 216, 234, 763, 764, 765, 766

[56] References Cited

U.S. PATENT DOCUMENTS

| | | | |
|---|---|---|---|
| 3,028,862 | 4/1962 | Prater, Jr. ............................ | 128/218 |
| 3,063,451 | 11/1962 | Kowalk ................................. | 128/221 |
| 3,330,282 | 7/1967 | Visser et al. ................. | 128/218 M X |
| 3,464,412 | 9/1969 | Schwartz ....................... | 128/218 M |
| 3,596,562 | 8/1971 | Winkelman .............................. | 128/2 |
| 3,809,298 | 5/1974 | Harris, Sr. et al. .................. | 222/386 |
| 3,848,581 | 11/1974 | Cinqualbre et al. .................... | 128/2 |
| 3,908,638 | 9/1975 | Porcher et al. .......................... | 128/2 |
| 3,930,492 | 1/1976 | Hatsuno et al. .......................... | 128/2 |
| 3,943,917 | 3/1976 | Johansen ................................. | 128/2 |
| 3,960,139 | 6/1976 | Bailey ..................................... | 128/2 |
| 3,978,846 | 9/1976 | Bailey ..................................... | 128/2 |
| 4,004,587 | 1/1977 | Jess ....................................... | 128/214 |
| 4,073,288 | 2/1978 | Chapman ................................ | 128/2 |
| 4,173,222 | 11/1979 | Muetterties ......................... | 128/214 |
| 4,206,768 | 6/1980 | Bailey ................................... | 128/763 |

Primary Examiner—John D. Yasko
Attorney, Agent, or Firm—Lockwood, Dewey, Alex & Cummings

[57] ABSTRACT

A syringe for collecting a blood sample includes a cylindrical housing having a hollow needle at one end. A plunger slidably mounted within the housing defines a chamber within which blood collected by the needle is received. A hydrophilic bypass element disposed between the rim of the plunger and the inside surface of the housing forms a passageway through which air is exhausted as blood enters the chamber under arterial pressure. The passageway is automatically closed to prevent leakage from the chamber when the chamber becomes filled with blood and the bypass element is wetted. An alternate embodiment wherein the hydrophilic bypass element is in the form of an annular sleeve extending around the rim of the plunger is shown.

28 Claims, 5 Drawing Figures

U.S. Patent  Jul. 20, 1982  Sheet 1 of 2  4,340,067
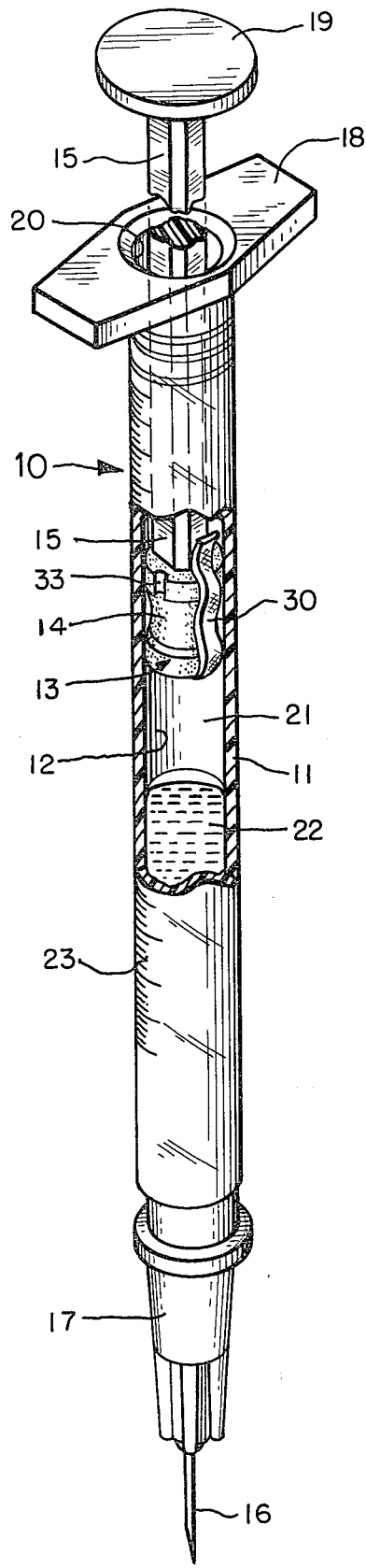
FIG. 1
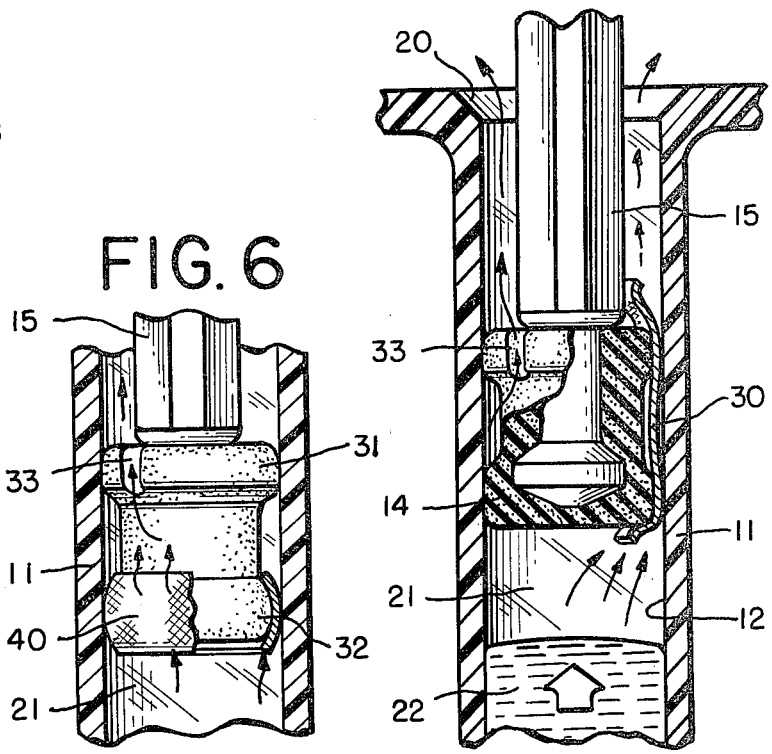
FIG. 2a
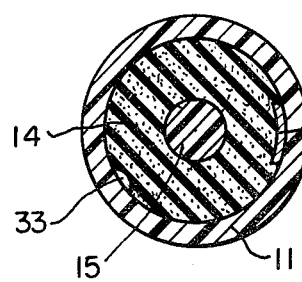
FIG. 6
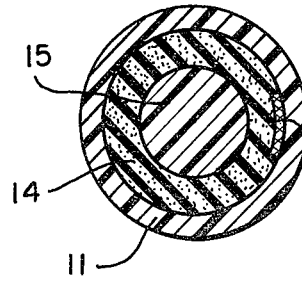
FIG. 3
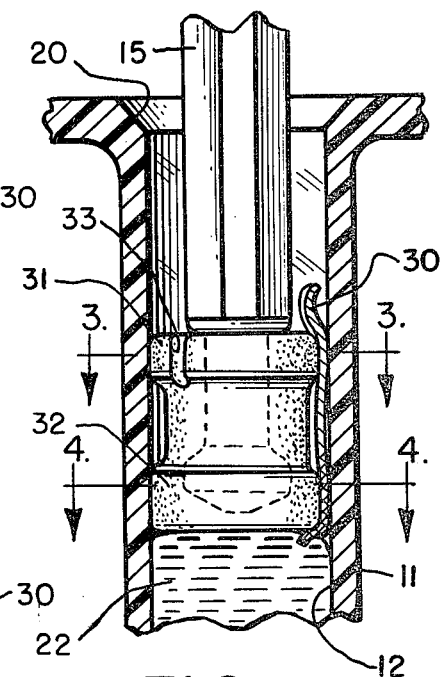
FIG. 4
FIG. 2b

BLOOD COLLECTION SYRINGE

BACKGROUND OF THE INVENTION

This application is directed generally to apparatus for collecting fluid samples, and more particularly to a syringe for collecting a blood sample from a human or animal blood vessel.

One method commonly used for collecting blood samples from the artery of a human is to puncture the artery by means of a conventional syringe needle with the piston of the syringe in an advanced position, and thereafter retract the piston to suck a blood sample into the chamber of the syringe. However, it is not always possible to ascertain whether an artery has been actually punctured before retracting the cylinder, with the result that the patient may be subject to discomfort and inconvenience as another attempt is made to puncture the artery. Furthermore, even after an artery has been punctured, it is difficult to keep the syringe still as the piston is retracted, with the result that the patient may experience further discomfort during the procedure.

An alternative procedure for collecting a blood sample utilizing a syringe is described in U.S. Pat. No. 3,943,917. This procedure contemplates that the piston of the syringe be prepositioned to form a collection chamber within the syringe. The syringe needle is then inserted into an artery, and blood from the artery is allowed to flow into the chamber while the piston remains stationary. A passageway formed by either a channel in the syringe housing or by the insertion of a wedge member in the form of a rod or tube to deform the piston seal allows air to escape from the chamber as blood enters the chamber. When the chamber has filled, the passageway is closed by repositioning the piston or by removing the wedge member, and the sample is dispensed as required by advancing the piston.

One disadvantage of this alternative procedure has been the necessity of the operator having to close the air escape passageway following collection of a blood sample. Where the passageway is formed in the syringe housing, this has necessitated advancing the piston to a position clear of the passageway, thereby decreasing the volume of the chamber and causing an undesired dispensing of blood through the syringe needle. Where the escape passageway is formed by deformation of the piston seal, the operator is required to locate and withdraw the wedge member after the wedge member has been in contact with the collected blood sample.

One proposed solution to the problem of closing the air escape passageway provides a length of string along one side of the piston to displace the piston seal. The outside end of the string is wound around the piston stem, which is rotatably mounted to the piston. To remove the string and thereby seal the collection chamber, the stem is twisted by the operator until the string is drawn clear of the piston seal. Like the previously described syringe apparatus, this apparatus requires attention and manipulation by the operator, and presents a risk of leakage as the string is removed.

The syringe apparatus of the present invention avoids the necessity of the operator having to manipulate the syringe to seal the collection chamber by providing an air relief passageway which is automatically closed upon the collection chamber filling with blood. This is done without attention by the operator, and without the possibility of leakage.

SUMMARY OF THE INVENTION

The invention is directed to a syringe for collecting a fluid sample from a fluid vessel. The syringe comprises an elongated hollow housing having a sidewall defining a central bore open at one end to the atmosphere, a hollow needle mounted on the other end of the housing, the needle having a central passageway in communication with the bore, and a plunger slidably mounted within the bore and forming in conjunction with the needle a fluid receiving chamber within the housing. Pressure relief means comprising a bypass element establish a pressure relief passageway between the chamber and the open end of the bore for gas trapped in the chamber, this passageway becoming closed to preclude leaking of fluid from the chamber upon the bypass element becoming wetted by fluid collected in the chamber.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 1 is a perspective view of a syringe constructed in accordance with the invention.

FIG. 2a is an enlarged cross-sectional view of the piston of the apparatus of FIG. 1 showing the provision of a hydrophilic bypass element along one side of the piston prior to the chamber of the syringe being filled with collected fluid.

FIG. 2b is a view similar to the view of FIG. 2a subsequent to the chamber filling with collected fluid.

FIG. 3 is a cross sectional view of the piston and syringe housing taken along line 3—3 of FIG. 2b.

FIG. 4 is a cross-sectional view of the piston and syringe housing taken along line 4—4 of FIG. 2b.

FIG. 6 is an enlarged side elevational view partially in cross-section illustrating an alternative form of construction of the syringe piston and associated bypass element.

DESCRIPTION OF THE PREFERRED EMBODIMENT

Figure 5A:
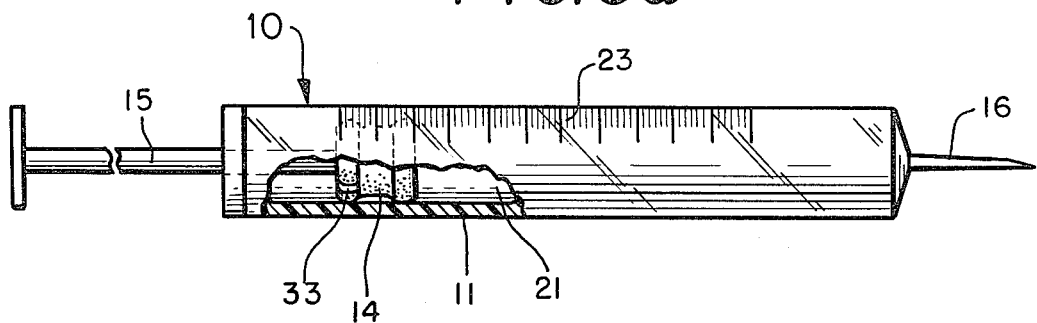
FIG. 5a is a simplified diagrammatic representation of the syringe with the piston prepositioned for use.

Referring to the figures, and particularly to FIG. 1, a syringe 10 constructed in accordance with the invention is seen to include a hollow generally cylindrical housing 11 formed of a suitable non-pyrogenic material such as plastic. The sidewall of housing 11 defines a bore 12 of generally uniform cross-section. Within bore 12 a piston assembly 13 consisting of a piston head 14 and a piston stem 15 is arranged for reciprocative movement along the axis of the housing.

At one end housing 11 is fitted with a needle assembly comprising a hollow syringe needle 16 and needle adaptor cap 17 in accordance with conventional practice. At the other end housing 11 may include a flange portion 18, and the stem 15 may include an enlarged end portion 19, to facilitate positioning of the piston assembly by a user in a manner well known to the art.

As thus far described, syringe 10 is entirely conventional in design. Blood may be drawn into the syringe through hollow needle 16 by retracting piston assembly 13, and may be forced from the syringe by extending the piston assembly toward the needle end of housing 11. In this regard it will be noted that the actuator end of housing 11, opposite the needle end, is open to the atmosphere, the piston stem 15 extending through an opening 20 for access by the user. In practice, the piston head 14 obtains a sliding liquid and air-sealed engagement with the inside wall 12 of housing 11, thereby forming a liquid and air sealed chamber 21 within the syringe wherein a fluid 22 such as blood is collected. The sidewall of housing 11 is preferably transparent to allow the user to view the liquid contained in the chamber, and appropriate indicia may be applied to the housing to enable the quantity of liquid collected to be ascertained.

Referring to FIGS. 2a and 2b, syringe 10 includes, in accordance with the invention, an air bypass element 30 which provides a controlled pressure relief passageway for air trapped in chamber 21. This element, which may comprise a thin strip of hydrophilic material, is wedged between the piston head 14 and the inside surface 12 of the sidewall of housing 11 so as to be movable with the piston head.

In accordance with conventional practice, the piston head 14 is provided with two axially spaced annular rim portions 31 and 32 (FIG. 2b) to obtain a double seal for chamber 21, and to render this seal substantially unaffected by lateral movement of stem 15.

In a preferred embodiment of the invention, the strip-shaped bypass element 30 is of sufficient length to extend across both rim portions 31 and 32, thereby being held more securely in place with reciprocative motion of piston assembly 13. Furthermore, to assist the bypass element 30 in relieving trapped air from chamber 21, rim portion 31 is preferably provided with an axially-extending channel 33 which serves to vent air from the annular space between rim portions 31 and 32. As seen in FIG. 2a, this channel effectively bypasses the air passageway formed by bypass element 30, but does not bypass the passageway formed by that element through rim portion 32. Thus, ultimate control of the flow of air from chamber 21 depends on the ability of bypass element 30 to pass air through rim portion 32.

In accordance with the invention, the bypass element 30 is formed of a porous hydrophilic material which allows the relatively free passage of gases such as air when dry, and which blocks the passage of gases when wet. This characteristic is relied on by the syringe of the invention to allow the free passage of trapped air from chamber 21 prior to the chamber being filled, as shown in FIG. 2a, and to preclude the passage of trapped air or fluid after the chamber has been filled by fluid and the bypass element has been wetted, as shown in FIG. 2b.

The ability of the syringe of the invention to automatically condition itself between venting and non-venting modes greatly simplifies the blood collection procedure, as illustrated in FIGS. 5a–5d.

Referring to FIG. 5a, the piston head 14 of syringe 10 is initially positioned to form a chamber 21 having a volume corresponding to the volume of blood to be collected. The scale 23 on the outside surface of housing 11 is useful for this purpose. Typically, the piston assembly may be positioned to collect a one cc. blood sample.

Figure 5B:
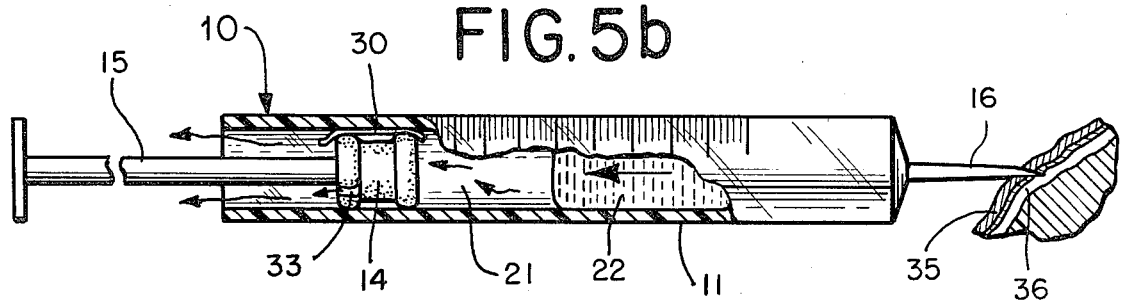
FIG. 5b is a simplified diagrammatic representation of the syringe showing the flow of blood into the syringe chamber under arterial pressure.

Next, as shown in FIG. 5b, the hollow needle 16 of syringe 10 is inserted through the skin 35 of a patient so as to pierce an underlying artery 36. At this point arterial pressure causes blood flow through needle 16 into chamber 21, the blood 22 progressively advancing toward the piston head 14. Air trapped within chamber 21 by the advancing blood is vented as previously described by bypass element 30 and chennel 33 around the rim portions of piston head 14. Since the trapped air is freely vented, the flow of blood 22 into chamber 21 is unhindered, and may progress as dictated by pressure in the arterial source. Since this unhindered flow is readily visible to the user through the transparent sidewall of housing 11, the user can readily ascertain when the blood advances in a pulsating flow that an artery has in fact been pierced.

Figure 5C:
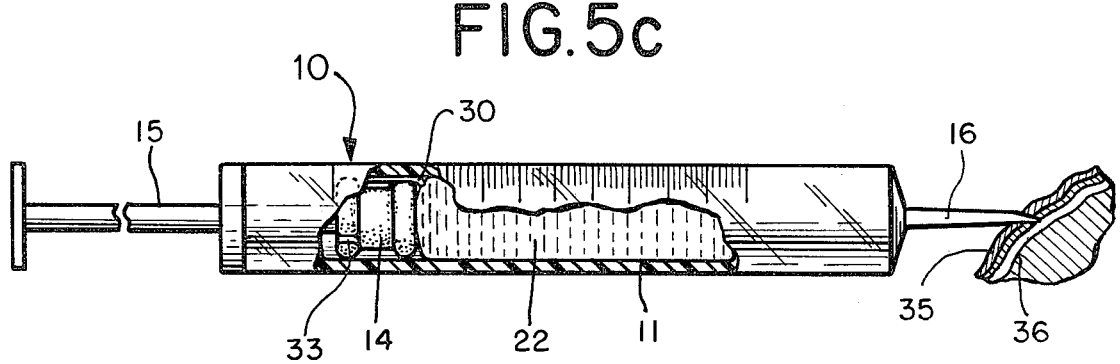
FIG. 5c is a simplified diagrammatic representation of the syringe following collection of a blood sample in the syringe chamber.

When collection chamber 21 has been completely filled by collected blood, as shown in FIG. 5c, bypass member 30 is wetted and is therefore no longer effective in venting gas from the chamber. The syringe can now be removed from the patient without the danger of leakage through the needle or through the pressure relief passageway, thereby avoiding any possibility of exposure of the user to the collected blood.

Figure 5D:
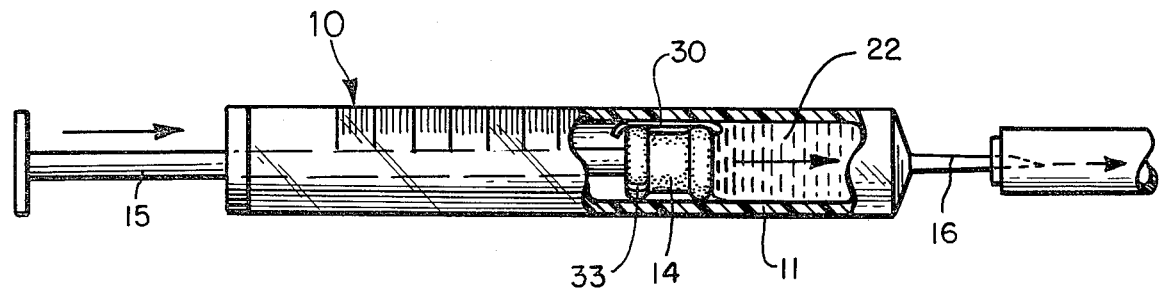
FIG. 5d is a simplified diagrammatic presentation of the syringe showing the discharge of a collected sample into a test chamber.

To transfer the collected blood from chamber 21 to blood analyzer apparatus, the syringe is inserted in the receiving receptacle of the apparatus, as shown in FIG. 5d, and the piston assembly is advanced by the user to force blood out of the chamber through needle 16. The entire volume of collected blood, or any portion thereof, may thus be conveniently transferred for analysis without the necessity of the user having to close a valve, remove a bypass element, or realign the piston head.

An alternative construction for the bypass element is shown in FIG. 6. In this embodiment of the invention the bypass element takes the form of an annular sleeve 40 of hydrophilic material fitted over the rim portion 32 of piston head 14. Thus positioned, the bypass element when dry provides a bypass for trapped air around the entire circumference of the piston head, allowing for a freer passage of air from chamber 21 than provided by the strip-line construction of the bypass element previously described. As in the previous embodiment, an axially extending channel 33 is provided in rim portion 31 to vent the annular space between the rim portions of the piston head.

Bypass elements 30 and 40 may be formed from various types of hydrophilic materials, such as porous filter papers, or copolymers of polyvinyl chloride and acrylonitrile placed on a nylon fabric substrate. Porous filter papers which have proven successful in this application are manufactured by Filpaco Industries, Inc. of Chicago, Ill., as type PW-36 and type PW-25 filter papers. Both of these papers have a filter size of four microns. One suitable copolymer material is sold by the Gelman Instrument Company of Ann Arbor, Mich., under the designation AN5000. It is contemplated that other filter materials having a pore size of 4–5 microns and of appropriate thickness may be utilized in blood collection applications.

While particular embodiments of the invention have been shown and described, it will be obvious to those skilled in the art that changes and modifications may be made without departing from the invention and its broader aspects, and, therefore, the aim in the appended claims is to cover all such changes and modifications as fall within the true spirit and scope of the invention.

I claim:

1. A fluid collection syringe, comprising, in combination:

an elongated hollow housing having a sidewall defining a central bore, said housing being open at one end to the atmosphere;

a hollow needle member mounted on the other end of said housing, said needle member having a central passageway in communication with said bore;

a plunger assembly including a plunger slidably mounted within said bore, said plunger assembly forming at least a partial sliding liquid and gas seal with said sidewall whereby said plunger assembly forms in conjunction with said other end of said housing a fluid receiving chamber within said bore having a volume dependent on the position of said plunger assembly; and said plunger assembly including pressure relief means comprising a bypass element disposed between said plunger and the inside surface of said sidewall for establishing a pressure relief passageway between said chamber and the atmosphere for air trapped in said chamber, said bypass element when dry allowing air to pass through said passageway to enable fluid entering said chamber through said needle member to displace air from said chamber through said passageway, and when wet blocking fluid from passing through said passageway, and remaining at least partially exposed to the interior of said chamber when said chamber is filled with fluid whereby said bypass element is wetted to prevent fluid from leaking from said chamber through said passageway.

2. A fluid sample collection syringe as defined in claim 1 wherein said bypass element is formed of a porous material, which allows the passage of air when dry and blocks the passage of said fluid when wetted by said fluid.

3. A fluid sample collection syringe as defined in claim 1 wherein said bypass element is in the form of a thin strip of porous material positioned between said plunger and the inside surface of said sidewall.

4. A fluid sample collection syringe as defined in claim 1 wherein said plunger includes at least one annular rim portion slidably engaged in gas-sealing relationship to said inside surface of said sidewall, and said bypass element is disposed between said rim portion and said sidewall.

5. A fluid sample collection syringe as defined in claim 4 wherein said plunger includes an additional rim portion between said at least one rim portion and the open end of said housing, said additional rim portion having an axially extending channel therein providing a gas passageway between said bypass element and the atmosphere.

6. A syringe as defined in claim 2 wherein said plunger includes at least one annular rim portion slidably engaged in gas-sealing relationship to the inside surface of said sidewall, and said bypass element comprises an annular collar disposed over said rim portion between said rim portion and the interior surface of said sidewall.

7. A fluid collection syringe, comprising, in combination:

an elongated hollow housing having a sidewall defining a central bore, said housing being open at one end to the atmosphere;

a hollow needle member mounted on the other end of said housing, said needle member having a central passageway in communication with said bore;

a plunger assembly including a plunger slidably mounted within said bore, said plunger assembly forming at least a partial sliding liquid and gas seal with said sidewall whereby said plunger assembly forms in conjunction with said other end of said housing a fluid receiving chamber within said bore having a volume dependent on the position of said plunger assembly; and said plunger assembly including pressure relief means comprising a bypass element formed of a thin strip of porous material positioned between said plunger and the inside surface of said sidewall, said bypass element allowing free passage of air from said chamber when dry and blocking the passage of fluid when wetted by said fluid, one end of said strip remaining at least partially exposed to the interior of said chamber following collection of a fluid sample therein, whereby said bypass element initially passes air from said chamber to allow fluid to enter said chamber through said needle member until said chamber becomes substantially filled, and thereafter is wetted by said fluid to block the passage of fluid to preclude fluid leaking from said chamber.

8. A syringe for collecting a blood sample from an artery, said syringe comprising, in combination:

an elongated generally cylindrical housing having a sidewall defining a central bore, said housing being open at one end to the atmosphere;

a hollow needle member mounted on the other end of said housing, said needle member having a central passageway in communication with said bore;

a plunger assembly including a plunger slidably mounted within said bore, said plunger assembly forming at least a partial sliding liquid and air seal with said sidewall whereby said plunger assembly forms in conjunction with said other end of said housing a blood receiving chamber within said bore having a volume dependent on the position of said plunger assembly; and said plunger assembly including pressure relief means comprising a bypass element disposed between said plunger and the inside surface of said sidewall for establishing a pressure relief passageway between said chamber and said open end of said bore for air trapped in said chamber, said bypass element when dry allowing the free passage of air from said chamber through said passageway to enable blood entering said chamber under arterial pressure through said needle member to displace air from said chamber, and when wetted by blood blocking the passage of blood through said passageway, and remaining at least partially exposed to the interior of said chamber when said chamber is filled with blood whereby said bypass element is wetted to preclude blood leaking from said chamber through said passgeway.

9. A blood sample collection syringe as defined in claim 8 wherein said plunger includes at least one annular rim portion slidably engaged in air-sealed relationship to said inside surface of said sidewall, and said bypass element is disposed between said rim portion and said sidewall.

10. A blood sample collection syringe as defined in claim 9 wherein said plunger includes an additional rim portion between said at least one rim portion and the open end of said housing, said additional rim portion having an axially-extending channel therein providing an air passageway between said bypass element and the atmosphere.

11. A syringe as defined in claim 8 wherein said plunger includes at least one annular rim portion slidably engaged in air sealing relationship to the inside surface of said sidewall, and said bypass element comprises an annular collar disposed over said rim portion between said rim portion and the interior surface of said sidewall.

12. A blood sample collection syringe as defined in claim 8 wherein said bypass element is formed of a porous material, which allows the passage of gas when dry and blocks the passage of blood when wetted by said blood.

13. A blood sample collection syringe as defined in claim 12 wherein said porous material comprises porous filter paper having a pore size of from four to five microns.

14. A syringe for collecting a blood sample from an artery, said syringe comprising, in combination:
   an elongated generally cylindrical housing having a sidewall defining a central bore, said housing being open at one end to the atmosphere;
   a hollow needle member mounted on the other end of said housing, said needle member having a central passageway in communication with said bore;
   a plunger assembly including a plunger slidably mounted within said bore, said plunger assembly forming at least a partial sliding liquid and air seal with said sidewall whereby said plunger assembly forms in conjunction with said other end of said housing a blood receiving chamber within said bore having a volume dependent on the position of said plunger assembly; and
   said plunger assembly including pressure relief means comprising a bypass element formed of a thin strip of porous material disposed between said plunger and the inside surface of said sidewall for establishing a pressure relief passageway between said chamber and said open end of said bore, said bypass element when dry allowing the free passage of air through said passageway to enable blood entering said chamber under arterial pressure through said needle member to displace air through said passageway, and when wetted by said blood blocking the passage of blood through said passageway, one end of said strip remaining at least partially exposed to the interior of said chamber following collection of a blood sample therein whereby said bypass element is wetted to preclude leaking of blood from said chamber.

15. A fluid collection syringe comprising, in combination:
   an elongated hollow housing having a sidewall defining a central bore, said housing being open at one end to the atmosphere;
   a needle member mounted on the other end of said housing, said needle member having a central passageway in communication with said bore;
   a plunger assembly slidably mounted within said bore, said plunger assembly including a plunger having a rim portion forming at least a partial sliding liquid and gas seal with said sidewall whereby said plunger assembly forms in conjunction with said other end of said housing a fluid receiving chamber within said bore having a volume dependent on the position of said plunger assembly; and
   said plunger assembly including pressure relief means comprising an annular bypass element disposed over said rim portion between said rim portion and the inside surface of said sidewall for establishing a pressure relief passageway between said chamber and the atmosphere for gas trapped in said chamber, said bypass element when dry allowing gas to pass from said chamber to allow fluid to enter said chamber through said needle member, and when wet blocking gas from passing from said chamber, and being at least partially exposed to the interior of said chamber whereby when said chamber is filled with fluid said bypass element is wetted to prevent fluid from leaking from the chamber.

16. A syringe as defined in claim 15 wherein said annular bypass element is formed of a hydrophilic material, which allows the passage of gas when dry and blocks the passage of gas and liquid when wetted by said fluid.

17. A syringe as defined in claim 15 wherein said plunger includes an additional rim portion having an axially-extending channel therein providing a gas passageway between said bypass element and the atmosphere.

18. A syringe for collecting a blood sample from an artery, said syringe comprising, in combination:
   an elongated generally cylindrical housing having a sidewall defining a central bore, said housing being open at one end to the atmosphere;
   a needle member mounted on the other end of said housing, said needle member having a central passageway in communication with said bore;
   a plunger assembly slidably mounted within said bore, said plunger assembly including a plunger having a rim portion forming at least a partial sliding liquid and air seal with side sidewall whereby said plunger assembly forms in conjunction with said other end of said housing a fluid receiving chamber within said bore having a volume dependent on the position of said plunger assembly; and
   said plunger assembly including pressure relief means comprising an annular bypass element disposed over said rim portion between said rim portion and the inside surface of said sidewall for establishing a pressure relief passageway between said chamber and said open end of said bore for air trapped in said chamber, said bypass element when dry allowing the free passage of air from said chamber to allow blood to enter said chamber under arterial pressure through said needle assembly, and when wetted by said blood blocking the passage of air and blood and being at least partially exposed to the interior of said chamber whereby when said chamber is filled with blood said bypass element is wetted to preclude leaking of blood from said chamber.

19. A syringe as defined in claim 18 wherein said annular bypass element is formed of a hydrophilic material, which allows the passage of air when dry and blocks the passage of air and liquid when wetted by said fluid.

20. A syringe as defined in claim 18 wherein said plunger includes an additional rim portion having an axially-extending channel therein providing an air passageway between said bypass element and the atmosphere.

21. A fluid sample collection syringe as defined in claim 2 wherein said porous material comprises a hydrophilic material.

22. A blood sample collection syringe as defined in claim 12 wherein said porous material comprises a hydrophilic material.

23. A blood sample collection syringe as defined in claim 8 wherein said bypass element is in the form of a thin strip of porous material positioned between said plunger and the inside surface of said sidewall.

24. A blood sample collection syringe as defined in claim 14 wherein said porous material comprises porous filter paper having a pore size of from four to five microns.

25. A fluid collection syringe comprising, in combination:
   an elongated hollow housing having a sidewall defining a central bore, said housing being open at one end to the atmosphere;
   a hollow needle member mounted on the other end of said housing, said needle member having a central passageway in communication with said bore;
   a plunger assembly including a plunger slidably mounted within said bore, said plunger assembly forming at least a partial sliding liquid and gas seal with said sidewall whereby said plunger assembly forms in conjunction with said other end of said housing a fluid receiving chamber within said bore having a volume dependent on the position of said plunger assembly; and
   said plunger assembly including pressure relief means comprising a bypass element disposed between said plunger and the inside surface of said sidewall for establishing a pressure relief passageway between said chamber and the atmosphere for exhausting air from said chamber upon fluid entering said chamber through said needle member, said pressure relief passageway automatically closing to the passage of fluid without movement of said plunger upon the chamber becoming filled with fluid.

26. A fluid sample collection syringe as defined in claim 25 wherein said bypass element is in the form of a thin strip of porous material positioned between said plunger and the inside surface of said sidewall.

27. A syringe for collecting a blood sample from an artery, said syringe comprising, in combination:
   an elongated generally cylindrical housing having a sidewall defining a central bore, said housing being open at one end to the atmosphere;
   a hollow needle member mounted on the other end of said housing, said needle member having a central passageway in communication with said bore;
   a plunger assembly including a plunger slidably mounted within said bore, said plunger assembly forming at least a partial sliding liquid and air seal with said sidewall whereby said plunger assembly forms in conjunction with said other end of said housing a blood receiving chamber within said bore having a volume dependent on the position of said plunger assembly; and
   said plunger assembly including pressure relief means comprising a bypass element disposed between said plunger and the inside surface of said sidewall for establishing a pressure relief passageway between said chamber and the atmosphere for exhausting air from said chamber upon blood entering said chamber through said needle member, said pressure relief passageway automatically closing to passage of blood without movement of said plunger upon said chamber becoming filled with blood.

28. A blood sample collection syringe as defined in claim 27 wherein said bypass element is in the form of a thin strip of porous material positioned between said plunger and the inside surface of said sidewall.

* * * * *

Disclaimer 4,340,067.—*Christen C. Rattenborg*, Chicago, Ill. BLOOD COLLECTION SYRINGE. Patent dated July 20, 1982. Disclaimer filed Aug. 9, 1985, by the assignee, *Marquest Medical Products, Inc.*

Hereby enters this disclaimer to claims 1, 2, 4, 6, 8, 9, 11, 12, 15, 18, 25 and 27 of said patent.

[*Official Gazette September 24, 1985.*]